United States Patent [19]

Mayor et al.

[11] Patent Number: 5,571,840

[45] Date of Patent: Nov. 5, 1996

[54] METHOD FOR TREATING CENTRAL NERVOUS SYSTEM ISCHEMIA

[75] Inventors: Gilbert H. Mayor, Lincolnshire, Ill.; Louis G. D'Alecy, Ann Arbor, Mich.

[73] Assignees: The Regents of the University of Michigan, Ann Arbor, Mich.; Knoll Pharmaceuticals Co., Mount Olive, N.J.

[21] Appl. No.: 254,417

[22] Filed: Jun. 6, 1994

Related U.S. Application Data

[63] Continuation of Ser. No. 79,805, Jun. 22, 1993, abandoned.

[51] Int. Cl.⁶ .................................................. A61K 31/195
[52] U.S. Cl. ............................................................ 514/567
[58] Field of Search ............................................... 514/567

[56] References Cited

U.S. PATENT DOCUMENTS 5,158,978  10/1992  Rubin ........................................ 514/567

FOREIGN PATENT DOCUMENTS 2240474  8/1991  United Kingdom.

OTHER PUBLICATIONS

Michel et al., Mal. Med./Drug Dis., 1 (1, Symp. Eur. Expressions Metab. Tissulaires Pathol. Cereb. I), 79–89. 1984.

Rami et al., Life Science, 50(9), 645–50. 1992.

Natale et al. "Effect of the Aminosteroid U74006F After Cardiopulmonary Arrest in Dogs." *Stroke* vol. 19, (1988) pp. 1371–1378.

Natale et al. "Protection From Cerebal Ischemia by Brain Cooling Without Reduced Lactate Accumulation in Drugs." *Stroke* vol. 20, (1989) pp. 770–777.

Natale et al. "Continued Circulatory Support: Effect of Epinephrine or Dopamine on 24 hour Survival and Neurologic Function in Dogs." *Resuscitation* vol. 17 (1989) pp. 273–286.

D'Alecy et al. "Dextrose Containing Intravenous Fluid Impairs Outcome and Increases Death After Eight Minutes of Cardiac Arrest and Resuscitation in Dogs." *Surgery* vol. 100 (1986) pp. 505–511.

Lundy et al. "Infusion of Five Percent Dextrose Increases Mortality and Morbidity Following Six Minutes of Cardiac Arrest in Resuscitated Dogs." *Journal of Critical Care* vol. 2 (1) (Mar. 1987) pp. 4–14.

Novitzky et al. "Triiodothyronine in the Recovery of Stunned Myocardium in Dogs." *Ann.Thorac.Surg.* vol. 51 (1991) pp. 10–17.

Novitzky et al. "Inotropic Effect of Triiodothyronine Following Myocardial Ischemia and Cardiopulmonary Bypass: An Experimental Study in Pigs." *Ann.Thorac.Surg.* vol. 45 (1988) pp. 50–55.

Garcia–Fages et al. "Effects of Substitutive Triiodothyronine Therapy on Intracellular Nucleotide Levels in Donor Organs." *Transplantation Proceedings* vol. 23 (1991) pp. 2495–2496.

Lindop. "Basic Principles of Donor Management for Multiorgan Removal." *Transplantation Proceedings* 23 (1991) pp. 2463–2464.

Montero et al. "Biochemical Hypothyroidism and Myocardial Damage in Organ Donors: Are they related?" *Transplantation Proceedings* vol. 20 (1988) pp. 746–748.

Orlowski et al. "The use of Thyroxine (T–4) to Promote Hemodyanamic Stability in the Vascular Organ Donor: A Preliminary Report on the Colorado Experience." *J.Transplant Coordination* vol. 1 (1991) pp. 19–22.

Henahan. "Does Thyroid Hormone Enhance Cardiac Patient Recovery?" *Hospital Pharmacist Report* (Jun. 1993) pp. 24–25 and 28.

Novitzky et al. "Triiodothyronine as an Inotropic Agent After Open Heart Surgery." *J.Thorac.Cardiovasc.Surg.* vol. 98 (1989) pp. 972–978.

Robuschi et al. "Cardiopulmonary Bypass: A low $T_4$ and $T_3$ Syndrome with Blunted Thyrotropin (TSH) Response to Thyrotropin–Releasing Hormone (TRH)." *Hormone Res.* vol. 23 (1986) pp. 151–158.

Weaver. "Resuscitation Outside the Hospital—What's Lacking?" *The New England Journal of Medicine* vol. 325 (1991) pp. 1437–1439.

Brain Resuscitation Clinical Trial II Study Group. "A Randomised Clinical Study of a Calcium–Entry Blocker (lidoflazine) in the Treatment of Comatose Survivors of Cardiac Arrest." *The New England Journal of Medicine* vol. 324 (1991) pp. 1225–1230.

Ceremuzynski. "Hormonal and Metabolic Reactions Evoked by Acute Myocardial Infarction." *Circulation Research* vol. 48 (1981) pp. 767–776.

Wartofsky et al. "Alterations in Thyroid Function in Patients with Systemic Illness: The Euthyroid Sick Syndrome." *Endocrine Reviews* vol. 3 (1982) pp. 164–217.

Plum. "Vulnerability of the Brain and Heart after Cardiac Arrest." *The New England Journal of Medicine* vol. 324 pp. 1278–1280 (1982).

Wortsman et al. "Hypothyroxinemia in Cardiac Arrest." *Archives of Internal Medicine* vol. 147 (1987) pp. 245–248.

Dulchavsky et al. "Triiodothyronine (T3) Improves Cardiovascular Function During Hemorrhagic Shock." *Circulatory Shock* vol. 39 (1993) pp. 68–73.

Ramaker et al. "Transthyretin—An Explanation of Anomalous Serum Thyroid Hormone Values in Severe Illness." *J.Clin.Chem.Clin.Biochem* vol. 28 (1990) pp. 155–161.

(List continued on next page.)

*Primary Examiner*—Phyllis G. Spivack
*Attorney, Agent, or Firm*—Nikaido, Marmelstein, Murray & Oram, LLP

[57] ABSTRACT

Central nervous system ischemia in a patient who has suffered an acute insult is treated by administering an effective amount of a thyroid hormone selected from the group levothyroxine, liothyronine, L-3,3',5'-triiodothyronine or L-3,5-diiodothyronine, or their sodium salts. The treatment is particularly applicable to the treatment of cerebral ischemia following cardiac arrest.

11 Claims, No Drawings

OTHER PUBLICATIONS

Chu et al. "Thyroid Hormone Changes After Cardiovascular Surgery and Clinical Implications." *Ann. Thorac. Surg.* vol. 52 (1991) pp. 791–796.

Dyke et al. "Triiodothyronine–Enhanced Left Ventricular Function After Ischemic Injury." *Ann. Thorac. Surg.* vol. 52 (1991) pp. 14–19.

Novitsky et al. "Triiodothyronine Therapy for Heart Donor and Recipient." *J.Heart Transplantation* vol. 7 No. 5 (1988) pp. 370–376.

Novitsky et al. "Improved Cardiac Allograft Function Following Triiodothyronine Therapy to Both Donor and Recipient." *Transplantation* vol. 49 No. 2 (1990) pp. 311–316.

Novitsky et al. "Inotropic Effect of Triiodothyronine (T3) in Low Cardiac Output Following Cardioplegic Arrest and Cardiopulmonary Bypass: an Initial Experience in Patients Undergoing Open Heart Surgery." *Eur.J.Cardio–Thorac. Surg.* vol. 3 (1989) pp. 140–145.

Koga et al. "Primary Hypothyroidism in Severe Chronic Heart Failure." *Jpn.J.Med.* vol. 27 No. 1 (1988) pp. 42–48.

Paschen et al. "Alteration in Thyroid Hormone Concentration During and After Coronary Bypass Operation." *Ann. Endocrinol.* vol. 44 No. 4 (1983) pp. 233–242.

Kranz et al. "The Influence of Hyperthyroidism and Hypothyroidism on the Wound Healing of Experimental Myocardial Infarction in the Rat." *Exp.Path.* vol. 12 (1976) pp. 129–136.

Gay et al. "Effects of 10– to 12–day Treatment with L–Thyroxine in Rats with Myocardial Infarction." *Am.J.Physiol.* vol. 255 (Heart Circ.Physiol.24) (1988) pp. H801–H806.

Gay et al. "Effects of L–Thyroxine in Rats with Chronic Heart Failure After Myocardial Infarction." *Am.J.Physiol.* vol. 253 (Heart Circ.Physiol.22) (1987) pp. H341–H346.

Novitsky et al. "Effect of Triiodothyronine ($T_3$) on Myocardial High Energy Phosphates and Lactate after Ischemia and Cardiopulmonary Bypass." *J.Thorac. Cardiovasc. Surg.* vol. 96 (1988) pp. 600–607.

Novitsky et al. "Triiodothyronine Therapy in the Cardiac Transplant Recipient." *Transplantation Proceedings* vol. XX No. 5 Suppl 7 (1988) pp. 65–68.

Michel et al. "Effects of Aging and Thyroid Status on Cerebral Subcellular Activity Levels. Experimental Study in the Rat." *Maladies et Medicaments* vol. 1 No. 1 (1984) pp. 79–89 English translation pp. 1–10.

Novitsky et al. "The Value of Triiodothyronine ($T_3$) in the Rescue of a Failing Heart Following Valve Replacement." From: The 23rd Annual Meeting of the Society of Thoracic Surgeans, 1987.

Abernethy. "Variability in human cardiovascular pharmacodynamics." *Advanced Methods of Pharmacokinetic and Pharmacodynamic Systems Analysis* (1991) pp. 69–77.

Abramson et al. "A randomised clinical study of a calcium–entry blocker (Lidoflazine) in the treatment of comatose survivors of cardiac arrest." *NEJM* vol. 324 (18), (1991) pp. 1225–1231.

Allen et al. "Thyroid hormone metabolism and level of illness severity in pediatric cardiac surgery patients." *J Pediatrics* vol. 114 (1989) pp. 59–63.

Aufderheide et al. "Milwaukee prehospital chest pain project . . . phase I feasibility and accuracy of prehospital thrombolytic candidate selection." *Am J Cardiol* vol. 69, (1992) pp. 991–996.

Bernstein et al. "Cardiac left ventricular function before and during early thyroxine treatment in severe hypothyoidism." *J Int Med* vol. 230, (1991) pp. 493–500.

Bremner et al. "Hypothalamo–pituitary–thyroid axis function during cardiopulmonary bypass." *J Thorac and Cardiovas Surg* vol. 75 (3), (1978) pp. 392–399.

Dazai et al. "Direct effect of thyroid hormone on left ventricular myocardial relaxation." *Japan Circ J* vol. 56, (1992) pp. 334–342.

Dillmann et al. "Molecular basis of thyroid hormone action in the heart." [Abstract] *Endocrine Society 74th Annual Meeting* Section 25E p. 45, 1992.

Ellyin et al. "Thyroid function in patients with post–traumatic stress syndrome." [Abstract] *The Endocrine Society 75th Annual Meeting* Las Vegas, NV (1993) p. 463.

Fazio et al. "Evaluation, by noninvasive methods, of the effects of acute loss of thyroid hormones on the heart." *J Vasc Diseases* (1992) pp. 287–293.

Feddersen et al. "Effects of cardiopulmonary bypass and prostacyclin on plasma catecholamines, angiotensin II and arginine–vasopressin." *Acta Anaesthesiol Sand* vol. 29, (1985) pp. 224–230.

Feldman et al. "Myocardial mechanics in hypothyroidism: importance of left ventricular loading conditions, heart rate, and contractile state." *JACC* vol. 7 (5), (1986) pp. 967–974.

Flattet et al. "Euthyroid sick syndrome." *Schweiz Med Wschr* vol. 116, (1986) pp. 169–172.

Hilberman et al. "The diuretic properties of dopamine in patients after open–heart operation." *Anesthes* vol. 61, (1984) pp. 489–494.

Holland et al. "Cardiopulmonary bypass and thyroid function: A 'euthyroid sick syndrome'." *Ann Thorac Surg* vol. 52, (1991) pp. 46–50.

Jarek et al. "Endocrine profile as a predictor of outcome in critical care patients." [Abstract] 1121 from *Endocrine Society 74th Annual Meeting* p. 332, 1992.

Ladenson et al. "Complications of surgery in hypothyroid patient." *Am Med* vol. 77, (1984) pp. 261–266.

Laragh. "The endocrine basis for human hypertension and its cardiovascular sequellae (heart attack and stroke)." [Abstract] *Endocrine Society 74th Annual Meeting* Section 25A, p. 41, 1992.

Leeson et al. "Selective thyromimetics. Cardiac–sparing thyroid hormo analogues containing 3'–arylmethyl substituents." *J Med Chem* vol. 32, (1989) pp. 320–336.

Maldonado et al. "Do thyroid function tests independently predict survival in the critically ill?" *Thyroid* vol. 2 (2), (1992) pp. 119–123.

McGregor. "Cardiac transplantation: Surgical considerations and early postoperative management." *Mayo Clin Proc* vol. 67 (1992) pp. 577–585.

Mintz et al. "Enhanced left ventricular diastolic function in hyperthyroidism: Noninvasive assessment and response to treatment." *J Clin Endo Metab* vol. 73 (1), (1991) pp. 146–150.

Mitchell et al. "The effects of cardiopulmonary bypass on thyroid function in infants weighing less than five kilograms." *J Thorac Cardiovasc Surg* vol. 103, (1992) pp. 800–805.

Parenteau et al. "New concepts in cardiopulmonary bypass." *Adv Cardi Surgery* vol. 3, (1991) pp. 9–56.

Philbin. "Endocrine response to cardiopulmonary bypass." *Mount Sinai Med* vol. 52 (7) (1985) pp. 508–510.

Reves. "Adrenergic response to cardiopulmonary bypass." *Mount Sinai Med* vol. 52 (7), (1985) pp. 511–515.

Roine et al. "Neuropsychological sequelae of cardiac arrest." *JAMA* vol. 269 (2), (1993) pp. 237–242.

Rosen et al. "Distinguishing hypothyroxinemia due to euthyroid sick syndrome from pituitary insufficiency." [Abstract] 339 *Endocrine Societ 74th Annual Meeting* p. 136, 1992.

Vitek et al. "Thyroid hormone responses in hemorrhagic shock: Study in dogs and preliminary findings in humans." *Surgery* vol. 93 (6), (1983) 771–777.

Woeber, "Thyrotoxicosis and the heart." *NEJM* vol. 327 (2), (1992) p. 98.

Yao et al. "Decreased collagen gene expression and absence of fibrosis in thyroid hormone–induced myocardial hypertrophy." *Circ Res* vol. 71, (1992) pp. 831–839.

METHOD FOR TREATING CENTRAL NERVOUS SYSTEM ISCHEMIA

This application is a continuation of application Ser. No. 08/079,805 filed Jun. 22, 1993, now abandoned.

This invention relates to the treatment of central nervous system ischemia. Examples of central nervous system ischemia include cerebral ischemia and spinal column ischemia. The central nervous system ischemia may result from an acute insult such as cardiac arrest (asystole and sustained ventricular arrythmias), hypoxemia, transient ischemic attack, stroke or severe hypotension.

The present invention provides a method of treating a patient suffering from central nervous system ischemia resulting from an acute insult, in which method a protective amount of one or more thyroid hormones is administered to the patient. The thyroid hormone may be administered as a single dose, as a continuous infusion or as an initial bolus dose followed by continuous infusion.

The thyroid hormone may be L-3,5,3',5'-tetraiodothyronine (levothyroxine or LT4) preferably in the form of its sodium salt (levothyroxine sodium), L-3,5,3'-triiodothyronine (liothyronine or LT3) preferably in the form of its sodium salt (liothyronine sodium), L- 3,3',5'-triiodothyronine (LrT3) preferably in the form of its sodium salt, L-3,5-diiodothyronine (LT2) preferably in the form of its sodium salt or mixtures thereof.

When the thyroid hormone is levothyroxine or a salt thereof, the amount of levothyroxine given as a single dose may lie in the range 500 to 5000 µg. The amount of levothyroxine administered by continuous infusion to the patient preferably lies in the range about 0.1 to about 15, preferably about 0.5 to about 10, more preferably about 1 to about 4 µg/kg/hr.

When the thyroid hormone is liothyronine or a salt thereof, the amount of liothyronine given as a single dose may lie in the range 30 to 2500 µg. The amount of liothyronine administered by continuous infusion to the patient preferably lies in the range about 0.01 to about 7.5, preferably about 0.03 to about 5, more preferably about 0.06 to about 1 µg/kg/hr.

When the thyroid hormone is LrT3 or a salt thereof, the amount of LrT3 given as a single dose may lie in the range 1000 to 10000 µg. The amount of LrT3 administered by continuous infusion to the patient preferably lies in the range about 0.2 to about 30, preferably about 1 to about 20, more preferably about 2 to about 8 µg/kg/hr.

The amount of thyroid hormone in the continuous infusion fluid is preferably such that the required dose is administered by the infusion of 0.1 to 10 ml/kg/hr of the infusion fluid.

The thyroid hormone is preferably administered by intravenous injection of a sterile solution of the thyroid hormone in a pharmaceutically acceptable solvent, for example saline solution. The solution may also contain other pharmaceutically acceptable components such as potassium and calcium chloride (Ringers solution USP) or pH-controlling agents.

For example, in a patient suffering from cardiac arrest the heart ceases to circulate blood around the body. The cessation of the pumping action of the heart stops the supply of blood to vital organs, such as the brain, and severe damage can be caused to those vital organs. It is therefore essential that any patient who suffers a cardiac arrest is resuscitated as soon as possible after the arrest so as to minimise the potential damage to vital organs. The medical profession is constantly seeking treatments which reduce the chances of this damage to vital organs occurring after cardiac arrest.

One preferred aspect of the present invention relates to a treatment to be administered to patients who have suffered a cardiac arrest to prevent or minimise cerebral ischemia. There are already many well established treatments which are given to patients following cardiac arrest, for example dopamine, dobutamine, lidocaine, isoproterenol, furosemide, heparin, mannitol, antibiotics (such as cefluroxime and imipenim/citastin) or vaopressin. It is intended that the treatment which forms the subject of the present invention should be additional to these established treatments.

The administration of the thyroid hormone should commence as soon as possible after the cardiac arrest. In a hospital situation where medical attention can be obtained very rapidly, the patient can be resuscitated and the administration of the thyroid hormone can be initiated within minutes. However, when the patient suffers cardiac arrest away from a hospital a much longer period of time will elapse before the patient can be resuscitated and the administration of the thyroid hormone can commence. It is however important that administration commences as soon as possible. Administration should be initiated as soon as the patient is receiving medical attention. If the patient is initially attended by a paramedic or ambulanceman then that person should initiate the administration before the patient is seen by a qualified medical practitioner. In a preferred method of treatment the patient who has suffered the cardiac arrest is initially given a bolus dose of the thyroid hormone. The initial bolus dose may be in the range of about 500 µg to about 5000 µg. Continuous infusion at the rates described above should then be initiated as soon as possible after the administration of the initial bolus dose.

Patients who have suffered a cardiac arrest are subject to careful monitoring by the medical practitioner responsible for their treatment. The administration of thyroid hormone will be stopped only when the medical practitioner believes that it is no longer beneficial to the patient. When the patient is in a stable haemodynamic and neurological situation, the medical practitioner may decide to cease administration of the thyroid hormone either immediately or, preferably, by means of a gradual reduction of the administered dose over a period of time. It is envisaged that after 18 to 24 hours the dose may start to be gradually reduced and that administration may cease after a further 24 to 48 hours if no adverse effects on the patient are observed.

The cerebral-protecting effect of the continuous administration of a thyroid hormone has been demonstrated by the following experiments performed on dogs. In the experiments each dog was anesthetised and surgically fitted with basic instrumentation, subjected to ventricular fibrillation to cause nine minutes of cardiac arrest and then resuscitated. Of the 33 dogs used 14 were not given any thyroid hormone and the remainder were continuously infused with either 7.5 µg/kg/hr or 15 µg/kg/hr of levothyroxine sodium over the experimental period of 24 hours.

Preparation of the Experimental Animals

Thirty-three fasted adult male mongrel dogs weighing between 14.5 and 24.1 kg were premedicated with 1.5 mg/kg s.c. morphine sulphate (Elkins-Sinn, Inc., Cherry Hill, N.J.) and anesthetised (Foregger Fluomatic, Smithtown, N.Y.) with 5% halothane (Halocarbon Laboratories, North Augusta, S.C.) in oxygen via face mask and demand ventilation. The dogs were mechanically ventilated (Air-Shields Ventimeter Ventilator, Hatboro, Penna.) with 1–2% halothane to maintain surgical anaesthesia and suppression of corneal reflexes. Paralysing agents were not used. Expired $CO_2$ tension was monitored and maintained between 4% and 5% (Beckman LB-2, Fullerton, Calif.). Deep esophageal temperature was monitored and maintained at 39.0°±1.0° C. before arrest and for at least one hour after resuscitation with a homeothermic blanket system (Model 50-7095, Harvard Apparatus, South Natick, Mass.). A urethral catheter was inserted to maintain an empty bladder.

Two venous catheters were inserted; one passed by way of the left external jugular vein to the right atrium for administration of resuscitation drugs, and the other into a muscular branch of the left femoral vein for fluid administration. Arterial blood pressure was measured through a catheter placed in a muscular branch of the left femoral vein for fluid administration. Arterial blood pressure was measured through a catheter placed in a muscular branch of the left femoral artery (Starham P23XL transducer, Gould, Inc., Oxnard, Calif.). Subcutaneous disk electrodes (Grass Instrument Co. E5SH Silver Cup Electrodes, Quincy, Mass.) were placed to monitor lead II electrocardiogram (ECG). Each animal received intravenously 500 ml of 0.45% sodium chloride (Abbott Laboratories, North Chicago, Ill.) with 1.5 meq/kg of sodium bicarbonate (Fisher Scientific, Fair Lawn, N.J.) To assure adequate hydration before arrest, followed by a continuous intravenous drip of 0.45% sodium chloride at 2 ml/kg/hr (IVAC 530, San Diego, Calif.) throughout the recovery period. A thoracotomy and pericardiectomy at the left fifth interspace facilitated direct cardiac compression. The correct placement of the jugular vein catheter was confirmed by direct palpation of the vena cava. All catheters and electrical leads were passed subcutaneously to exit the skin in the dorsal midscapular region for later attachment to a dog jacket and hydraulic/electric swivel. Pulsatile and mean arterial blood pressure (MAP), ECG, and end-expiratory $CO_2$ were continuously recorded on a six-channel oscillograph (Model 200, Gould-Brush, Cleveland, Ohio).

Cardiac Arrest

At the conclusion of surgical instrumentation, halothane was discontinued while ventilation was continued with room air (Model 607, Harvard Apparatus, South Natick, Mass.) in order to reduce and standardize the level of anaesthesia at which ventricular fibrillation was induced. As soon as corneal reflexes returned (stage 3, plane 1 of surgical anaesthesia), the heart was fibrillated by delivering a 10–15 second, 60 Hz, 2 msec square-wave stimulus to the left ventricular epicardium. Ventilation was discontinued while circulatory arrest was confirmed by ECG, MAP, and direct observation of the heart.

Resuscitation

After 9 minutes of normothermic ventricular fibrillation, ventilation was restarted while direct cardiac massage maintained MAP above 75 mmHg. Vasopressor support was initiated by central venous administration of 40 μg/kg epinephrine (Berlex Laboratories, Inc., Wayne, N.J.) and 10 μg/kg/min dopamine (Abbott Laboratories), followed in rapid succession by 1 mg/kg lidocaine (Elkins-Sinn, Inc.), 4 meq/kg sodium bicarbonate, and 25 mg/kg calcium chloride (American Regent Laboratories, Inc., Shirley, N.Y.). Cardioversion was attempted by delivering a 20–50 J charge (Lifepak 6 defibrillator/monitor, Physio Control, Redmond, Wash.) with 31 cm² paddles placed on the right and left ventricular surfaces. Additional drugs or charges were administered as indicated by MAP and ECG monitoring.

Post-resuscitation dopamine infusion maintained MAP above 75 mmHg as long as necessary but for not longer than 6 hours (typically only 30 min). A rubber catheter was passed through the chest wall and sealed in place with a purse string suture; intermittent suction (Gomco Thoracic Pump, Gomco Corp., Buffalo, N.Y.) was used to evacuate any air or fluid accumulation after chest closure. Mechanical ventilation continued until spontaneous ventilation ensued, but for not longer than 6 hours (typically only 30 min). Extubation occurred upon return of the gag reflex.

Four dogs were not placed on the room air ventilator subsequent to completion of the surgical preparation, but were instead maintained on 0.5% halothane. The heart was fibrillated. Upon confirmation of ventricular fibrillation, cardioversion was attempted immediately; resuscitation drugs were administered only as indicated. This group is identified below as the control group. Halothane/oxygen was replaced with room air ventilation after chest closure. In this way, these animals received the full extent of the surgical insult while sustaining the shortest possible period of ventricular fibrillation and resuscitation. The three other experimental groups were subjected to a controlled 9 min cardiac arrest, in contrast to the control, which had minimum ischemia (approx. 30 sec) but otherwise identical surgical manipulations.

All dogs were given 10 mg/kg i.m. Spectinomycin (Ceva Laboratories, Inc., Overland Park, Kans.). No animals in this study exhibited behaviours that required post-operative analgesia. Each dog was placed in a jacket and swivel (Alice King Chatham Medical Arts, Los Angeles, Calif.) permitting 3 electrical and 3 hydraulic connections while allowing free movement about the cage. Dogs surviving to 24 hours post-arrest were killed with 120 mg/kg i.v. sodium pentobarbital following final neurologic deficit scoring and blood sampling. Post-mortem examinations of the heart, lungs, and wound sites were conducted to identify iatrogeny and heart worm infestations. Animals were excluded from this study if their cause of death could be attributed to any cause (haemorrhage, pneumothorax, catheter placement, etc.) other than neurologic impairment.

Blood Sampling

Ten arterial blood samples were taken for thyroid hormones, pH, hematocrit and plasma glucose measurement. The first sample was drawn immediately after the insertion of femoral artery catheter and served as the baseline. Ventilation and bicarbonate administration were then manipulated as needed during surgery to maintain arterial blood pH between 7.38 and 7.41 (pH/Blood Gas Analyser 113, Instrumentation Laboratories, Lexington, Mass.). Plasma glucose concentrations were determined by the glucose oxidase method using an automated glucose analyzer (YSI Model 23A, Yellow Springs, Ohio). Hematocrit measurements were made using standard microcentrifuge tubes. The second sample was taken immediately before the induction of ventricular fibrillation (pre-arrest), and the third sample was taken immediately after the animal was resuscitated (post-arrest). The remaining samples were taken 0.5, 1, 2, 4, 6, 12 and 24 hours post-arrest. At each sample time, the MAP, heart rate (HR), and body temperature (mid-esophageal while on the operating table; rectal when placed in a recovery cage) were noted. Total urine output was also noted until the bladder catheter was removed (not later than 6 hours post-arrest).

Thyroid Hormone Assay

At all ten sample times, arterial blood samples for the thyroid assays (total thyroxine, T4; free thyroxine, FT4; total 3,5,3'-triiodothyronine, T3; free 3,5,3'-triiodothyronine, FT3; and reverse 3,3',5'-triiodothyronine, rT3) were withdrawn into clot activated sample tubes (Vacutainer SST 6510, Becton Dickinson, Rutherford, N.J.) and allowed to clot at room temperature for 30 minutes before they were centrifuged at 1300 g for 10 minutes. The serum was removed and stored at −20° C. The thyroid hormones were assayed using standard radioimmunoassay methods.

Neurologic Deficit Assessment

A well-standardized score was assigned 1, 2, 6, 12 and 24 hours post-arrest to assess neurologic deficit. Interobserver variability was resolved through consultation of the detailed description of each neurologic functional level. Of the 100 points possible, 18 are assigned to consciousness, 18 to respiratory function, 16 to cranial nerve function, 20 to spinal nerve function, and 28 to motor function as set out in Table 1.

TABLE 1

|  | Score |
|---|---|
| CONSCIOUSNESS (Range 0–18) | |
| Normal, consistently alert | 0 |
| Continually conscious but clouded | 3 |
| Intermittently conscious, aroused with minimum effort | 6 |
| Stuporous, aroused with persistent effort | 12 |
| Light coma, reflex movement only | 15 |
| Deep coma, no movement | 18 |
| RESPIRATION (Range 0–18) | |
| Normal, extubated and normal | 0 |
| Extubated/abnormal, extubated but normal | 6 |
| Intubated/spontaneous, intubated but off ventilator | 12 |
| On ventilator, intubated and on ventilator | 18 |
| CRANIAL NERVES (Range 0–16) | |
| Corneal reflex | |
| Strong, consistently blinks in response or saline in eye area | 0 |
| Weak, inconsistently blinks in response to touch or saline in eye area | 1 |
| Absent, does not respond to touch or saline in eye area | 2 |
| Pupillary light reflex | |
| Strong, constricts pupil to light quickly and completely | 0 |
| Weak, constricts pupil to light slowly and/or incompletely | 1 |
| Absent, does not constrict pupil to light or pupil fixed and constricted | 2 |
| Facial sensation | |
| Strong, reacts consistently to touch in any area of face | 0 |
| Weak, reacts to touch only in certain areas or inconsistently | 1 |
| Absent, does not react to touch in any facial area | 2 |
| Gag reflex | |
| Strong, rapid and strong reaction to endotracheal tube or forceps in throat | 0 |
| Weak, slow, weak, inconsistent reactior | 1 |
| Absent, no gag response on stimulation of throat | 2 |
| Jaw reflex | |
| Strong, strongly resists rapid opening of jaw | 0 |
| Weak, weakly resists rapid opening of jaw | 1 |
| Absent, jaw flaccid | 2 |

TABLE 1-continued

|  | Score |
|---|---|
| Pinna reflex | |
| Strong, twitches ear in response to touch on outer/inner hairs | 0 |
| Weak, twitches ear in response to touch on deep inner hairs only | 1 |
| Absent, does not move ear in response to touch | 2 |
| Olfactory reflex | |
| Strong, strong reaction to acetic acid near nostril | 0 |
| Weak, weak reaction to acetic acid near nostril | 1 |
| Absent, no reaction | 2 |
| Swallowing reflex | |
| Strong, consistently swallows water when injected into mouth | 0 |
| Weak, inconsistent swallowing of water | 1 |
| Absent, does not swallow | 2 |
| SPINAL NERVES (Range 0–20) | |
| Limb tone (fore/hind) | |
| Normal, limb has tone without stiffness | 0/0 |
| Spastic, stiff tone; resists movement | 2/2 |
| Flaccid, no tone | 4/4 |
| Pain reflex (fore/hind) | |
| Strong, quick, complete withdrawal from toe pinch | 0/0 |
| Weak, slow, incomplete, or inconsistent withdrawal from toe pinch | 2/2 |
| Absent, no withdrawal from toe pinch | 4/4 |
| Knee jerk | |
| Strong, normal slow response | 0 |
| Weak, incomplete response | 2 |
| Absent, no response or hyper-reflexive | 4 |
| MOTOR FUNCTION (Range 0–28) | |
| Normal, walks normally | 0 |
| Minimal ataxia, walks with some impairment of gait | 2 |
| Ataxia, just able to walk | 4 |
| Stands spontaneously, falls with a few steps | 6 |
| Stands if posed, falls with any movement | 8 |
| Sits spontaneously, without falling | 10 |
| Sits if posed, falls with any movement | 12 |
| Spontaneous dorsal recumbancy | 14 |
| Posed dorsal recumbancy | 16 |
| Spontaneous purposeful movement, unprovoked, nonconvulsive movement | 18 |
| Provoked purposeful movement, provoked non-convulsive movement | 20 |
| Preflex, spastic, or convulsive movement only | 24 |
| No movement | 28 |

Protocols and Experimental Groups

The animals in this study were divided into four separate groups as outlined below. There are no differences among the groups in terms of the general preparation or instrumentation before the induction of cardiac arrest.

Controls

Four dogs received not more than 30 seconds of ventricular fibrillation (as described above) before resuscitative efforts were begun. These animals received no therapy or medications other than those described in the basic preparation.

Untreated

The 10 dogs in the untreated group received 9 minutes of normothermic ventricular fibrillation before resuscitative efforts were begun. These animals received no therapy or medications other than those described in the basic preparation.

Treated-7.5

The 11 dogs in the treated-7.5 group received 9 minutes of normothermic ventricular fibrillation, exactly as in the untreated group. Immediately following initial cardiopulmonary resuscitation, however, the treated-7.5 group received a constant infusion of 7.5 µg/kg/hr levothyroxine sodium (L-T4; Boots Pharmaceuticals, Inc., Lincolnshire, Ill.) for the duration of the recovery period (24 hours) via the central venous catheter. No other therapy or medications were administered to the treated dogs in this group other than those described above in respect of their preparation and resuscitation.

Treated-15

The 8 dogs in the treated-15 group were identical to the treated-7.5 group with the exception that they received 15 µg/kg/hr L-T4 post-arrest. No other therapy or medications were administered to the treated dogs in this group other than those described above in respect of their preparation and resuscitation.

Statistical Calculations

Comparisons of all physiologic variables were assessed with one way analysis of variance (ANOVA-Scheffe). Neurologic deficit scores were compared nonparametrically using the Mann-Whitney U analysis. An unpaired, 2-tailed Student's t-test was used to assess differences in thyroid hormones between groups at the 12 hour time point (chosen because it was the last sample time at which all dogs were alive and at which the data were the most consistent). Differences in thyroid hormone within groups were assessed between the prearrest and 12 hour samples with a paired, 2-tailed Student's t-test. Ten individual hormone samples out of a total of 1650 were greater than 2 standard deviations from the mean of their respective groups and are not included in the analysis. All average data are expressed as mean ±1 standard error of the mean (SEM). All statistical calculations were performed on a Macintosh II computer using the Statview SE+Graphics™ software package.

All animals in all groups survived to at least 12 hours post-arrest. Average hours of survival were 24.0±0.0 (controls), 22.0±1.0 (untreated), 21.4±1.2 (treated-7.5), and 21.2±1.6 (treated-15), and were not found to be statistically different by the Fishers' exact test.

Thyroid Hormones

A statistically significant, rapid and sustained decrease in total T4, free T4, total T3, and free T3 was detected by paired Student's t-analyses in both the control and untreated groups following resuscitation. Both the untreated ($p<0.001$) and control ($p<0.072$) groups simultaneously showed an acute elevation in reverse T3.

Total and free T4 in the treated-7.5 and treated-15 groups showed significant and sustained elevations following resuscitation. Total and free T3 values, however, differed markedly among the groups. Despite thyroid hormone supplementation, the treated-7.5 group still exhibited significant decreases in both total and free T3. The T3 values in the treated-15 group varied as indicated by larger standard errors; at 12 hours post-arrest both the total and free T3 concentrations in the treated-15 group are significantly elevated above pre-arrest levels (as well as being significantly higher than any of the other groups at 12 hours. Only in the treated-15 group was the plasma concentration of total and free T3 within or above the normal ranges for these hormones during the 24 hours following cardiac resuscitation. Thyroid hormone supplementation increased reverse T3 levels in both the treated-7.5 and treated-15 groups not only above intra-group pre-arrest levels, but above nontreated groups as well ($p=0.0001$).

Neurologic Deficit

The neurological deficit scores obtained by each dog is set out below:

| Controls | | | | | |
|---|---|---|---|---|---|
| Dog No. | 1 hour | 2 hour | 6 hour | 12 hour | 24 hour |
| 592 | 7 | 3 | 0 | 0 | 3 |
| 599 | 3 | 3 | 0 | 2 | 0 |
| 582 | 25 | 19 | 0 | 0 | 0 |
| 573 | 21 | 14 | 7 | 0 | 0 |

| Untreated | | | | | |
|---|---|---|---|---|---|
| Dog No. | 1 hour | 2 hour | 6 hour | 12 hour | 24 hour |
| 598 | 66 | 61 | 25 | 34 | dead |
| 600 | 66 | 69 | 45 | 56 | dead |
| 587 | 61 | 62 | 34 | 31 | 44 |
| 588 | 64 | 61 | 29 | 41 | dead |
| 614 | 70 | 70 | 27 | 53 | dead |
| 619 | 60 | 60 | 29 | 24 | 26 |
| 604 | 66 | 65 | 27 | 20 | 24 |
| 608 | 66 | 73 | 45 | 45 | 31 |
| 574 | 71 | 70 | 54 | 43 | 41 |
| 572 | 64 | 72 | 36 | 42 | 34 |

| Treated 7.5 | | | | | |
|---|---|---|---|---|---|
| Dog No. | 1 hour | 2 hour | 6 hour | 12 hour | 24 hour |
| 603 | 66 | 68 | 24 | 23 | dead |
| 602 | 70 | 66 | 25 | 22 | dead |
| 607 | 61 | 68 | 28 | 21 | 25 |
| 606 | 71 | 67 | 29 | 62 | 48 |
| 605 | 62 | 60 | 23 | 22 | dead |
| 594 | 63 | 58 | 24 | 19 | 33 |
| 593 | 66 | 64 | 26 | 22 | 24 |
| 591 | 57 | 57 | 26 | 23 | 23 |
| 595 | 62 | 57 | 25 | 10 | dead |
| 596 | 66 | 67 | 29 | 31 | 31 |

| Treated 15 | | | | | |
|---|---|---|---|---|---|
| Dog No. | 1 hour | 2 hour | 6 hour | 12 hour | 24 hour |
| 597 | 66 | 68 | 23 | 20 | 19 |
| 617 | 67 | 64 | 29 | 34 | 27 |
| 621 | 67 | 64 | 28 | 35 | dead |
| 618 | 70 | 66 | 34 | 35 | dead |
| 616 | 63 | 63 | 28 | 22 | 26 |
| 615 | 66 | 63 | 34 | 35 | 46 |
| 611 | 66 | 66 | 37 | 19 | 24 |

|         | Treated 15 |        |        |         |         |
| Dog No. | 1 hour | 2 hour | 6 hour | 12 hour | 24 hour |
| --- | --- | --- | --- | --- | --- |
| 612 | 65 | 62 | 23 | 21 | 23 |
| 613 | 72 | 70 | 27 | 19 | dead |

All dogs survived the first 12 hours post-arrest, but the treated-7.5 group showed the greatest neurologic improvement of the three 9 minute cardiac arrest groups, gaining statistical significance by Mann-Whitney U (nonparametric) at 6 and 12 hours post-arrest compared to the untreated group. The treated-15 group showed statistically significant improvement compared to the control group at 12 hours post-arrest. The control group, despite heavy doses of morphine, 30 minutes of halothane anaesthesia, a thoracotomy/pericardiectomy, and an acute episode of ventricular fibrillation and cardiopulmonary resuscitation, showed completely restored neurologic function by 12 hours.

At 24 hours, if analysis includes all dogs dead=100 neurologic deficit score) there is no statistically significant separation among the 9 min arrest groups. Of the 11 dogs that died before 24 hours post-arrest, all 4 in the treated-7.5 group and 2 out of the 3 in the treated-15 group died suddenly of apparent cardiac pump failure or fibrillation in a manner unlike the more classical neurologic seizures leading to the deaths observed in the control group and in many previous studies using the same basic model. Excluding these "non-neurological deaths" and pooling the two treated groups (to increase sample size) allows for statistical separation from the control group at 24 hours post-arrest. Without pooling, the treated-7.5 group at 24 hours post-arrest (n=7) still shows a statistically significant improvement when compared to the untreated group (p= 0.031), but the treated-15 group (n=6) was no longer significantly different when compared to the control group (p=0.19).

We claim:

1. A method for treating a patient suffering from central nervous system ischemia resulting from an acute insult, comprising administering an effective amount of levothyroxine to the patient as a bolus dose and/or continuous infusion at a time consisting of after ischemia has occurred.

2. A method as claimed in claim 1 wherein levothyroxine is administered in the form of its sodium salt.

3. A method as claimed in claim 1 wherein levothyroxine or its sodium salt is continuously administered in an amount which lies in the range about 0.1 to 15 µg/kg/hr.

4. A method as claimed in claim 3 wherein the amount of levothyroxine which is continuously administered lies in the range about 0.5 to about 10 µg/kg/hr.

5. A method as claimed in claim 3 wherein the amount of levothyroxine which is continuously administered lies in the range about 1 to about 4 µg/kg/hr.

6. A method as claimed in claim 1 wherein an initial bolus dose of levothyroxine is administered to the patient before the initiation of the continuous infusion of levothyroxine.

7. A method as claimed in claim 6 wherein the levothyroxine comprising the bolus dose is levothyroxine sodium.

8. A method as claimed in claim 6 wherein the levothyroxine or its sodium salt comprising the initial bolus dose lies in the range about 500 µg to about 5000 µg.

9. A method as claimed in claim 6 wherein levothyroxine or its sodium salt is continuously administered in an amount which lies in the range about 0.1 to about 15 µg/kg/hr.

10. A method as claimed in claim 9 wherein the amount of levothyroxine which is continuously administered lies in the range about 0.5 to about 10 µg/kg/hr.

11. A method as claimed in claim 9 wherein the amount of levothyroxine which is continuously administered lies in the range about 1 to about 4 µg/kg/hr.

* * * * *